United States Patent [19]
Akemi et al.

[11] Patent Number: 5,650,165
[45] Date of Patent: Jul. 22, 1997

[54] PERCUTANEOUS ABSORPTION PREPARATION

[75] Inventors: Hitoshi Akemi; Takateru Muraoka; Kazuhiro Higashio; Yutaka Suzuki; Saburo Otsuka, all of Osaka, Japan

[73] Assignee: Nitto Denko Corporation, Osaka, Japan

[21] Appl. No.: 551,786

[22] Filed: Nov. 7, 1995

[30] Foreign Application Priority Data

Nov. 15, 1994 [JP] Japan ................ 6-280342

[51] Int. Cl.$^6$ ............ A01N 29/02; A61K 31/035; A61L 15/16; A61F 13/02
[52] U.S. Cl. ............ 424/448; 424/447; 514/946; 514/947
[58] Field of Search .......... 424/447, 448, 424/449; 128/155, 156, 260, 268; 514/946, 947

[56] References Cited

U.S. PATENT DOCUMENTS

| | | | |
|---|---|---|---|
| 3,797,494 | 3/1994 | Zaffaroni | 128/268 |
| 5,128,124 | 7/1992 | Fankhauser et al. | 424/449 |
| 5,242,951 | 9/1993 | Akemi et al. | 514/772.5 |
| 5,298,258 | 3/1994 | Akemi et al. | 424/484 |
| B1 3,598,122 | 11/1982 | Zaffaroni | 128/268 |

FOREIGN PATENT DOCUMENTS

| | | |
|---|---|---|
| 0435200 | 7/1991 | European Pat. Off. . |
| 0513832 | 11/1992 | European Pat. Off. . |
| 0531938 | 3/1993 | European Pat. Off. . |
| 0680754 | 11/1995 | European Pat. Off. . |
| WO07951 | 9/1989 | WIPO . |

OTHER PUBLICATIONS

Chemical Abstracts, vol. 112, No. 16, Apr. 16, 1990.

*Primary Examiner*—Thurman K. Page
*Assistant Examiner*—Kathryne E. Shelborne
*Attorney, Agent, or Firm*—Sughrue, Mion, Zinn, Macpeak & Seas

[57] ABSTRACT

This invention provides a percutaneous absorption preparation for use in the percutaneous administration of drugs for percutaneous absorption into the living body for the purpose of preventing or treating various diseases, which has excellent adhesion to the skin and does not cause pain and damage to corneum when peeled off. Its pressure-sensitive adhesive layer contains an acrylic copolymer comprising a (meth) acrylic acid alkyl ester and a functional monomer as essential components, a fatty acid ester having a specified number of carbon atoms, a monoglyceride having a specified number of carbon atoms and a drug for percutaneous absorption, and the pressure-sensitive adhesive layer is crosslinked. Since its skin adhesive property is improved by the inclusion of the monoglyceride, release of the drug from the preparation is improved and the area of the preparation can be miniaturized.

5 Claims, No Drawings

PERCUTANEOUS ABSORPTION PREPARATION

FIELD OF THE INVENTION

This invention relates to percutaneous absorption preparations, more particularly to a percutaneous absorption preparation which not only can effect durable and quick absorption of a drug for percutaneous absorption into the body by simply adhering it to the skin surface, but also exerts excellent adhesion to the skin surface applied and does not cause a pain or damage to stratum corneum when stripped from the skin surface.

BACKGROUND OF THE INVENTION

In recent years, various skin adhesive type external preparations such as poultices, tapes and the like have been developed as percutaneous absorption preparations for use in the administration of drugs into the living body through the skin surface. Among them, tapes that contain drugs capable of exerting systemic pharmacological actions are particularly worthy of notice.

Under such actual circumstances, tape type percutaneous absorption preparations have been proposed, developed and partly put into practical use, in which nitroglycerin, isosorbide dinitrate or other drug selected from various steroids, non-steroidal drugs, anesthetic agents, antihypertensive drugs and the like is included in the pressure-sensitive adhesive layer as a pharmacologically active substance. These percutaneous absorption preparations comprises an acrylic or synthetic rubber pressure-sensitive adhesive and a drug for percutaneous absorption mixed therein, and by only placing these percutaneous absorption preparations on the skin surface, the drug is continuously absorbed in a body through the skin surface, thereby providing excellent pharmacological actions.

However, since these preparations are those to be adhered to the skin surface, they have a possibility of causing an eruption on the adhered area of the skin due to irritation and the like when used for a prolonged period of time. That is, the conventional percutaneous absorption preparation generally has a pressure-sensitive adhesive having relatively strong adhesive property or is entirely overcoated with a pressure-sensitive adhesive sheet having strong adhesive property and fixed to the skin through the adhesive property of the sheet, in order to fix the preparation to the skin area securely. When skin adhesion is increased in such a manner, transfer of a drug contained therein to skin (skin transfer) will be improved in general, but there is a possibility that corneous cells on the skin surface applied are damaged on peeling the preparation to remove, and significant skin irritation is caused when the preparation is continuously used for a prolonged period of time repeatedly exchanging it with fresh ones.

For the purpose of reducing such strong adhesion-induced skin irritation, a so-called gel percutaneous absorption preparation has been proposed for example in JP-A-3-220120 (the term "JP-A" as used herein means an "unexamined published Japanese patent application"). This preparation, of which an acrylic pressure-sensitive adhesive layer contains a relatively large amount of oily liquid components having high compatibility so as to impart a soft feeling of touch to the pressure-sensitive adhesive layer, is an epoch-making percutaneous absorption preparation which can reduce skin irritation during its application to the skin due to the soft pressure-sensitive adhesive layer and can be removed smoothly after its use without causing damage to the stratum corneum.

However, since these adhesive type percutaneous absorption preparations are used by adhering them to the skin surface, it is necessary to maintain a balance of their skin adhesion and skin irritation, while simultaneously exerting proper transfer to skin and percutaneous absorption of a drug contained therein. It therefore is an ultimate future object to develop a percutaneous absorption preparation which can satisfy all of these necessities.

The aforementioned preparation of JP-A-3-220120 can exert excellent effects which cannot be found in other conventional percutaneous absorption preparations, but it still has room for improvement in terms of its skin adhesion. In addition, it is desirable to make the size (area) of each percutaneous absorption preparation as small as possible in order to reduce skin irritation, but this preparation also has room for improvement in terms of securing skin adhesion when its area is minimized, as well as skin transfer and percutaneous absorption of drugs.

SUMMARY OF THE INVENTION

With the aim of overcoming the above-described problems, the inventors of the present invention have conducted intensive studies and found that the above-described problems can be resolved when specified fatty acid ester and monoglyceride are added as liquid components to an acrylic copolymer in which a (meth)acrylic acid alkyl ester is used as the main monomer, and its pressure-sensitive adhesive layer is crosslinked. The present invention has been accomplished on the basis of this finding.

According to the present invention, there is provided a percutaneous absorption preparation comprising a backing and a pressure-sensitive adhesive layer containing a drug for percutaneous absorption formed on one side of the backing, wherein the pressure-sensitive adhesive layer contains (1) an acrylic copolymer prepared by copolymerization of a monomer mixture comprising a (meth)acrylic acid alkyl ester and a functional monomer as essential components, (2) a fatty acid ester comprising a higher fatty acid having 12 to 16 carbon atoms and a lower monohydric alcohol having 1 to 4 carbon atoms, (3) a monoglyceride comprising a higher fatty acid having 8 to 10 carbon atoms and glycerol and (4) a drug for percutaneous absorption (excluding isosorbide dinitrate), and the pressure-sensitive adhesive layer is crosslinked.

Other objects and advantages will be made apparent as the description progresses.

DETAILED DESCRIPTION OF THE INVENTION

Preferred examples of the backing to be used in the percutaneous absorption preparation of the present invention include those which do not cause reduction of the content of a fatty acid ester, a monoglyceride and a drug for percutaneous absorption contained in the pressure-sensitive layer due to their permeation through the backing into its back side. Examples of such a backing include single films and laminate films of polyester, nylon, Saran, polyethylene, polypropylene, polyvinyl chloride, ethylene-ethyl acrylate copolymer, polytetrafluoroethylene, Surlyn (produced by Du Pont), and metallic foil. In order to obtain proper adhesive force (anchoring force) between the backing and the pressure-sensitive adhesive layer, it is desirable to prepare the backing as a laminate of a non-porous plastic film and a porous film made of the above materials. In that case, it is desirable to form the pressure-sensitive adhesive layer on the porous film side.

Examples of the porous film include those which can improve anchoring force with the pressure-sensitive adhesive layer, such as paper, woven fabric, non-woven fabric, and mechanically punched sheet. Paper, woven fabric or non-woven fabric is particularly preferred from the standpoint of easy handling and the like. It is preferred that the porous film has a thickness of from 10 to 500 µm from the standpoint of anchoring force improvement, flexibility of the preparation as a whole and adhesion handling, or of from 10 to 200 µm in the case of a thin preparation such as a plaster type or pressure-sensitive tape type preparation. When woven or non-woven fabric is used as the porous film, it is preferred that it has a basis weight of from 5 to 30 g/m$^2$, more preferably from 6 to 15 g/m$^2$. The thickness of the non-porous plastic film is generally from 0.5 to 20 µm, preferably from 1 to 12 µm, more preferably from 1 to 6 µm.

According to the percutaneous absorption preparation of the present invention, the pressure-sensitive adhesive layer to be formed on one side of the aforementioned backing is a crosslinked structure having appropriate elasticity, namely a gel form, which contains a drug for percutaneous absorption, an acrylic copolymer, a fatty acid ester and a monoglyceride as the essential components and possesses proper skin adhesive force and cohesive force. The pressure-sensitive adhesive layer of the present invention shows an adhesive force of 80 to 250 g/24 mm width at room temperature (23±1° C.) when measured as its adhesive force to a bakelite plate by a measuring method which will be described later.

The acrylic copolymer to be used as the main base material of the pressure-sensitive adhesive layer of the present invention shows compatibility with the fatty acid ester and monoglyceride and has a proper skin adhesion and a property to maintain shape of the pressure-sensitive adhesive layer. Generally used pressure-sensitive adhesives such as natural rubber-based pressure-sensitive adhesives (e.g., natural rubber and synthetic rubber) and silicone-based pressure-sensitive adhesives are undesirable in the present invention, because these adhesives have insufficient compatibility with fatty acid esters and monoglycerides, and solubility and releasing property of drugs for percutaneous absorption are significantly low. Also, such pressure-sensitive adhesives have another problem in that it is difficult to adjust quantity of functional groups which take part in the crosslinking reaction and to carry out reproducible crosslinking treatment, as compared with the acrylic copolymer to be used in the present invention.

Such an acrylic copolymer can be obtained by using a (meth)acrylic acid alkyl ester usually used in acrylic pressure-sensitive adhesives as the main monomer component and copolymerizing the same with a functional monomer.

Examples of the (meth)acrylic acid alkyl ester which can be used include (meth)acrylic acid alkyl esters which have straight- or branched-chain alkyl groups having 4 to 13 carbon atoms, such as butyl, pentyl, hexyl, heptyl, octyl, nonyl, decyl, undecyl, dodecyl, and tridecyl. These esters may be used alone or as a mixture of two or more thereof.

The (meth)acrylic acid alkyl ester is not particularly limited to the above examples, and a (meth)acrylic acid alkyl ester having an alkyl group of 1 to 3 carbon atoms or a (meth)acrylic acid alkyl ester having an alkyl group of 14 or more carbon atoms may be used together as long as it does not alter characteristics of the present invention.

Examples of the functional monomer which can be copolymerized with the (meth)acrylic acid alkyl ester include those having at least one unsaturated double bond which participates in copolymerization reaction in one molecule and a functional group on its side chain such as a carboxyl group (e.g., (meth)acrylic acid, itcconic acid, maleic acid, and maleic anhydride), a hydroxyl group (e.g., (meth)acrylic acid hydroxyethyl ester, and (meth)acrylic acid hydroxypropyl ester), a sulfoxyl group (e.g., styrene sulfonate, allyl sulfonate, sulfopropyl ( meth ) acrylate, (meth) acryloyloxynaphthalene sulfonate, and acrylamidomethylpropane sulfonate), an amino group (e.g., (meth)acrylic acid aminoethyl ester, (meth)acrylic acid dimethylaminoethyl ester, and (meth)acrylic acid tert-butylaminoethyl ester), an amido group (e.g., (meth)acrylamide, dimethyl (meth)acrylamide, N-butyl acrylamide, N-methylol (meth)acrylamide, and N-methylolpropane (meth)acrylamide) and an alkoxyl group (e.g., (meth)acrylic acid methoxyethyl ester, (meth)acrylic acid ethoxyethyl ester, (meth)acrylic acid methoxyethylene glycol ester, (meth)acrylic acid methoxydiethylene glycol ester, (meth)acrylic acid methoxypolyethylene glycol ester, (meth)acrylic acid methoxypolypropylene glycol ester, and (meth)acrylic acid tetrahydrofurfuryl ester). Other examples of the functional monomer which can be copolymerized with the (meth)acrylic acid alkyl ester include (meth) acrylonitrile, vinyl acetate, vinyl propionate, N-vinyl-2-pyrrolidone, methyl vinyl pyrrolidone, vinyl pyridine, vinyl piperidone, vinyl pyrimidine, vinyl piperazine, vinyl pirazine, vinyl pyrrole, vinyl imidazole, vinyl caprolactam, vinyl oxazole, and vinyl morpholine.

These monomers may be used alone or as a mixture of two or more in the copolymerization. It is most preferred that at least one of the carboxyl group-containing monomers and hydroxyl group-containing monomers may be used as the essential component and if desired, the other monomers are additionally used, in view of adhesive and cohesive properties as pressure-sensitive characteristics, releasing property of the drug for percutaneous absorption contained in the pressure-sensitive adhesive layer and reactivity when the pressure-sensitive adhesive layer is crosslinked. Depending on each purpose, the copolymerization amount of the functional monomer can be set generally in the range of from 2 to 40% by weight, preferably from 3 to 35% by weight, based on the weight of the total monomers to be used for preparing the acrylic copolymer.

The acrylic copolymer can be prepared, for example, by dissolving the monomers and a known polymerization initiator in an organic solvent such as ethyl acetate and toluene, controlling the temperature of the mixture to 60±2° C. to conduct polymerization for several hours, and subsequently increasing the temperature to 80° C. to conduct ripening for several hours to tens hours.

It is preferred that the acrylic copolymer has a number average molecular weight of 10,000 to 200,000, more preferably from 50,000 to 1,000,000.

A fatty acid ester and a monoglyceride to be blended in the pressure-sensitive adhesive layer of the present invention are liquid (or in waxy form) at ordinary temperature, have compatibility with the aforementioned acrylic copolymer and are uniformly distributed in the pressure-sensitive adhesive layer. As the result, these components show a function to plasticize the pressure-sensitive adhesive layer, thereby rendering possible addition of softness to the pressure-sensitive adhesive layer and reduction of pain and skin irritation caused by the skin adhesive force when the percutaneous absorption preparation of the present invention is removed from the skin surface. In addition, since the pressure-sensitive adhesive layer is plasticized as described above, free diffusion of the drug for percutaneous absorption contained therein becomes appropriate and its release to the skin surface (skin transfer property) is also improved.

The fatty acid esters and monoglycerides having a function to plasticize the pressure-sensitive adhesive layer can be used in the present invention, but there is a possibility that those comprising fatty acids having too many or too little carbon atoms have poor compatibility with the aforementioned acrylic copolymer and vaporize during a heating step of the production process of the preparation. Also, there is a possibility that a fatty acid ester or a monoglyceride which comprises a fatty acid having a double bond in the molecule causes oxidation decomposition, thus entailing poor preservation stability. In addition, in the case of the percutaneous absorption preparation of the present invention, crystals of the drug for percutaneous absorption exceeding its saturated solubility are formed in the preparation when the drug content per unit area is large, but certain types of fatty acid esters and monoglycerides inhibit crystallization of the drug or delay its crystallization rate, thus causing a poor appearance of the resulting preparation or exerting a bad influence upon its preservation stability.

Therefore, a fatty acid ester composing a higher fatty acid having 12 to 16, preferably 12 to 14, carbon atoms and a lower monohydric alcohol having 1 to 4 carbon atoms is used as the fatty acid ester of the present invention. Preferred examples of such a higher fatty acid include lauric acid ($C_{12}$), myristic acid ($C_{14}$) and palmitic acid ($C_{16}$), with myristic acid being more preferred. Examples of the lower monohydric alcohol include methyl alcohol, ethyl alcohol, propyl alcohol and butyl alcohol, which may be either straight chain or branched-chain alcohols. Isopropyl alcohol is more preferably used. Consequently, the most preferred fatty acid ester is isopropyl myristate.

On the other hand, a monoglyceride comprising a higher fatty acid having 8 to 10 carbon atoms and glycerol is used as the monoglyceride of the present invention. Preferred examples of such a higher fatty acid include caprylic acid (octanoic acid, $C_8$), pelargonic acid (nonanoic acid, $C_9$) and captic acid (decanoic acid, $C_{10}$). The most desirable monoglyceride is caprylic acid monoglyceride.

According to the percutaneous absorption preparation of the present invention, the fatty acid ester and the monoglyceride are used generally in a total amount of from 60 to 200 parts by weight, preferably from 70 to 180 parts by weight, per 100 parts by weight of the acrylic copolymer. The blending ratio (by weight) of the fatty acid ester to the monoglyceride is generally in the range of from 1:0.05 to 1:0.25, preferably from 1:0.065 to 1:0.24, and more preferably from 1:0.08 to 1:0.18. In this connection, it is desirable that each of the fatty acid ester and the monoglyceride to be used has a high purity of 85% or more, because changes in the above blending ratio exert influence upon the effects of the present invention extremely delicately.

If the total content and blending ratio of the fatty acid ester and monoglyceride are outside the above ranges, there is a possibility that practical skin adhesion and low skin irritation cannot be obtained and release (skin transfer) of the drug for percutaneous absorption becomes insufficient. These problems become frequent as the size (area) of the percutaneous absorption preparation as a final product becomes small.

In addition to the aforementioned fatty acid ester and monoglyceride, other organic liquid components may be included in the pressure-sensitive adhesive layer if desired. In that case, these additional components may be used within such a range that they do not inhibit pressure-sensitive property of the preparation and releasing property of the drug for percutaneous absorption. Illustrative examples of such organic liquid components include glycols such as ethylene glycol, diethylene glycol, triethylene glycol, polyethylene glycol, propylene glycol, polypropylene glycol and the like, oils and fats such as olive oil, castor oil, squalene, lanolin and the like, organic solvents such as ethyl acetate, ethyl alcohol, 1,3-butanediol, dimethyldecyl sulfoxide, methyloctyl sulfoxide, dimethyl sulfoxide, dimethyl formamide, dimethyl acetamide, dodecyl pyrrolidone, isosorbitol, oleic acid and the like, liquid surface active agents and hydrocarbons such as liquid paraffin.

The pressure-sensitive adhesive layer of the percutaneous absorption preparation of the present invention is produced by blending a drug for percutaneous absorption with the aforementioned acrylic copolymer, fatty acid ester and monoglyceride as essential components and making the mixture into a gel by an appropriate crosslinking means, thereby effecting prevention of the outflow of fatty acid ester, monoglyceride and the liquid components contained therein and imparting cohesive force to the pressure-sensitive adhesive layer. The crosslinking can be conducted to such a degree that cohesive failure and remarkable reduction of the adhesive force of the pressure-sensitive adhesive layer are not caused. The crosslinking reaction may be effected by physical crosslinking making use of a radiation exposure such as of ultraviolet rays, electron rays or the like or by chemical crosslinking using a crosslinking agent such as a polyisocyanate compound, an organic peroxide, an organic metal salt, a metal alcoholate, a metal chelate compound, a polyfunctional compound or the like. When a radiation irradiation or an organic peroxide is used as the crosslinking means, decomposition reaction occurs under certain conditions. On the other hand, where highly reactive isocyanate compounds, usually used metal salts or organic metal salts are used, there is a possibility that coating workability in preparing the pressure-sensitive adhesive layer becomes poor because of the increment of solution viscosity after blending. Alternatively, a polyfunctional monomer such as a diacrylate may be copolymerized by blending it in advance at the time of the preparation of the acrylic copolymer. Also in this method, there is a possibility that the solution viscosity is increased at the time of polymerization. In the present invention, a trifunctional isocyanate, a metal alcoholate such as alcoholates of titanium or aluminum, or a metal chelate compound can be most preferably used from the standpoint of reactivity and easy handling. These crosslinking agents are markedly excellent in workability, because they do not cause increment of solution viscosity until coating and drying. The crosslinking agent is used in an amount of approximately from 0.01 to 2.0 parts by weight per 100 parts by weight of the acrylic copolymer. After coating and drying the composition for preparation of the pressure-sensitive adhesive layer which contains the crosslinking agent, the crosslinking can be conducted, for example, by heat-treating the layer at a temperature of 40° to 70° C. for several hours to tens hours.

The pressure-sensitive adhesive layer generally has a thickness of 20 to 200 μm, preferably from 30 to 150 μm, more preferably from 40 to 100 μm.

The drug for percutaneous absorption to be contained in the pressure-sensitive adhesive layer of the percutaneous absorption preparation of the present invention can be selected arbitrarily, depending on each therapeutic purpose, from percutaneously absorbable drugs which do not remain on the skin surface but exert local or systemic actions by penetrating under the skin or into blood, such as corticosteroids, analgesic anti-inflammatory agents, hypnoticsedatives, tranquilizers, antihypertensives, hypotensive diuretics, antibiotics, anesthetics, antimicrobial agents, antifungal agents, vitamins, coronary vasodilators, antihistaminics, antitussives, sex hormones, antidepressants, cerebral circulation improving agents, antiemetics, antitumor drugs, biomedics and the like. If desired, these drugs may be used as a mixture of two or more. From the standpoint of uniform dispersion in the pressure-sensitive adhesive layer and percutaneous absorption property, it is preferable to use fat-soluble drugs (solubility, 4 g or less per 100 ml water at ordinary temperature). Particularly preferred examples of the drug include estrogens (e.g., estradiol), nifedipine, ketoprofen and clonidine.

The content of these drugs for percutaneous absorption can be set at will depending on each drug to be used and object of its administration, and they are contained in the pressure-sensitive adhesive layer generally in an amount of from 1 to 40% by weight, preferably from 3 to 30% by weight based on the amount of the pressure-sensitive adhesive layer. If the content is smaller than 1% by weight, there is a possibility that the drug is not released in an amount effective for treatment or prevention purpose. If it is larger than 40% by weight, there is a possibility that the amount increased does not provide any further effect and rather results in economical disadvantage and inferior adhesive property to the skin. In the present invention, it is not necessary to dissolve entire portion of the drug in the pressure-sensitive adhesive layer, and the drug may be included in an amount exceeding its solubility in the pressure-sensitive adhesive layer so that a portion of the drug remains undissolved. In that case, the undissolved portion of the drug should be dispersed uniformly so that there is no fluctuation of the drug content in the percutaneous absorption preparation.

As a matter of course, the drug can be included in an amount outside the above range when it is necessary to impart a long-term sustained release property to the percutaneous absorption preparation, to increase releasing amount of the drug by increasing its content per unit area or to miniaturize the preparation for the purpose of reducing skin irritation.

As described above, the percutaneous absorption preparation of the present invention comprises a construction such that a crosslinked pressure-sensitive adhesive layer contains a drug for percutaneous absorption, an acrylic copolymer as a base material for supporting the drug for percutaneous absorption, and specified fatty acid ester and monoglyceride which have compatibility with the copolymer. As a result, the pressure-sensitive adhesive layer is provided with softness while keeping its cohesive force, so that the preparation hardly causes either irritation during its application to the skin surface or skin irritation caused by damage to the corneous cells in the applied area of the skin when the preparation is removed. Because of this, markedly good balance of its pressure-sensitive characteristics and low skin irritation can be obtained and excellent pharmacological effects can be expected. In this connection, when quantity of corneous separation at the time of the removal of the percutaneous absorption preparation of the present invention from the skin surface of volunteers was analyzed using a spectrophotometer as an index of painless removal of the preparation from the skin surface, the quantity of corneous separation caused by the preparation of the present invention was found to be $\frac{1}{5}$ to $\frac{2}{3}$ of that of a comparative preparation containing no fatty acid ester and monoglyceride, thus clearly showing advantages of the preparation of the present invention in pains on removing and skin adhesion.

In addition, since the pressure-sensitive adhesive layer of the percutaneous absorption preparation of the present invention is a so-called gel structure, diffusion transfer of the drug for percutaneous absorption contained therein has a large degree of freedom and its release therefore becomes good. Furthermore, since the blending of the monoglyceride renders possible excellent adhesion of the preparation to the irregular skin surface, the skin adhesion area increases and the drug release (skin transfer) is improved while maintaining the skin adhesion.

EXAMPLES

The present invention will now be illustrated in greater detail with reference to Examples, but it should be understood that the present invention is not deemed to be limited thereto. Unless otherwise indicated, all percents, parts, ratios and the like are by weight.

Preparation of Acrylic Copolymer A

In an atmosphere of an inert gas, 72 parts of 2-ethylhexyl acrylate, 25 parts of N-vinyl-2-pyrrolidone and 3 parts of acrylic acid were subjected to copolymerization in ethyl acetate to obtain a solution of acrylic copolymer A.

Preparation of Acrylic Copolymer B

In an atmosphere of an inert gas, 95 parts of 2-ethylhexyl acrylate and 5 parts of acrylic acid were subjected to copolymerization in ethyl acetate to obtain a solution of acrylic copolymer B.

Preparation of Acrylic Copolymer C

In an atmosphere of an inert gas, 70 parts of 2-ethylhexyl acrylate, 25 parts of vinyl acetate and 5 parts of 2-hydroxyethyl methacrylate were subjected to copolymerization in ethyl acetate to obtain a solution of acrylic copolymer C.

In order to reduce residual monomers, each of the thus obtained, copolymer solutions was coated on a separating paper in such an amount that the coat layer had a dry thickness of 100 µm and then dried at 100° C. for 10 minutes, and the thus treated acrylic copolymer was recovered and dissolved again in ethyl acetate to be used in the following examples.

Inventive Examples and Comparative Examples

Viscous solutions of compositions for use in the formation of pressure-sensitive adhesive layers were prepared using the formulations shown in Tables 1 to 4, and each of the thus prepared solutions was coated on a polyester separator (75 µm in thickness) in such an amount that the film layer has a dry thickness of 60 µm and then dried to obtain a pressure-sensitive adhesive layer. Thereafter, the thus obtained pressure-sensitive adhesive layer was applied to the non-woven fabric side of a laminate film made of a polyester non-woven fabric (basis weight, 8 g/m$^2$) and a polyester film (2 µm in thickness). In this manner, products of Inventive and Comparative Examples were prepared.

In this case, a crosslinking agent was blended in an amount of 0.4 part (copolymer A), 0.15 part (copolymer B) or 0.3 part (copolymer C) per 100 parts (as a solid content) of each acrylic copolymer, and the resulting pressure-sensitive adhesive layer was applied to the backing (laminate film) as described above and then subjected to heat aging at 70° C. for 60 hours.

TABLE 1

| No. | Acrylic polymer % | ES % | Fatty acid ester % | Mono-glyceride % | Cross-linking agent | Remarks |
|---|---|---|---|---|---|---|
| Inventive Examples | | | | | | |
| 1 | A 41.7 | 3.3 | IPM 52 | GMC 3 | C/HL | |
| 2 | " | " | IPM 51 | GMC 4 | " | |
| 3 | " | " | IPM 50 | GMC 5 | " | |
| Comparative Examples | | | | | | |
| 1 | A 41.7 | 3.3 | IPM 48 | GMC 7 | C/HL | |
| 2 | " | " | IPM 55 | — | " | |
| 3 | " | " | OP 50 | GMC 5 | " | |
| 4 | " | " | MITD 50 | " | " | |
| 5 | " | " | EO 50 | " | " | |
| 6 | " | " | IPM 50 | GMO 5 | " | |
| 7 | " | " | " | GML 5 | " | |
| 8 | A 96.7 | " | — | — | — | (a) |
| 9 | A 81.7 | " | IPM 12 | GMC 3 | C/HL | |
| 10 | A 41.7 | " | IPM 50 | GMC 5 | — | (b) |
| 11 | PIB 96.7 | " | — | — | — | |

TABLE 2

| No. | Acrylic polymer % | NP % | Fatty acid ester % | Mono-glyceride % | Cross-linking agent | Remarks |
|---|---|---|---|---|---|---|
| Inventive Examples | | | | | | |
| 4 | A 45 | 15 | IPM 37 | GMC 3 | C/HL | |
| 5 | " | " | IPM 35 | GMC 5 | " | |
| 6 | " | " | IPM 33 | GMC 7 | " | |
| Comparative Examples | | | | | | |
| 12 | A 45 | 15 | IPM 40 | — | C/HL | |
| 13 | " | " | OP 35 | GMC 5 | " | |
| 14 | " | " | MITD 35 | " | " | |
| 15 | " | " | EO 35 | " | " | |
| 16 | " | " | IPM 35 | GMO 5 | " | |
| 17 | " | " | " | GML 5 | " | |
| 18 | A 70 | " | IPM 12 | GMC 3 | " | |
| 19 | PIB 85 | " | — | — | — | |

TABLE 3

| No. | Acrylic polymer % | KP % | Fatty acid ester % | Mono-glyceride % | Cross-linking agent | Remarks |
|---|---|---|---|---|---|---|
| Inventive Examples | | | | | | |
| 7 | B 50 | 10 | IPM 37 | GMC 3 | C/HL | |
| 8 | " | " | IPM 35 | GMC 5 | " | |
| 9 | " | " | IPM 33 | GMC 7 | " | |
| Comparative Examples | | | | | | |
| 20 | B 50 | 10 | IPM 40 | — | C/HL | |
| 21 | " | " | OP 35 | GMC 5 | " | |
| 22 | " | " | MITD 35 | " | " | |
| 23 | " | " | EO 35 | " | " | |
| 24 | " | " | IPM 35 | GMO 5 | " | |
| 25 | " | " | " | GML 5 | " | |
| 26 | B 90 | " | — | — | — | |
| 27 | B 75 | " | IPM 12 | GMC 3 | C/HL | |
| 28 | B 50 | " | IPM 35 | GMC 5 | — | (b) |
| 29 | PIB 90 | " | — | — | — | |

TABLE 4

| No. | Acrylic polymer % | CD % | Fatty acid ester % | Mono-glyceride % | Cross-linking agent | Remarks |
|---|---|---|---|---|---|---|
| Inventive Examples | | | | | | |
| 10 | C 45 | 10 | IPM 42 | GMC 3 | C/HL | |
| 11 | " | " | IPM 40 | GMC 5 | " | |
| 12 | " | " | IPM 38 | GMC 7 | " | |
| Comparative Examples | | | | | | |
| 30 | C 45 | 10 | IPM 45 | — | C/HL | |
| 31 | " | " | OP 40 | GMC 5 | " | |
| 32 | " | " | MITD 40 | " | " | |
| 33 | " | " | EO 40 | " | " | |
| 34 | " | " | IPM 40 | GMO 5 | " | |
| 35 | " | " | " | GML 5 | " | |
| 36 | C 90 | " | — | — | — | |
| 37 | C 75 | " | IPM 12 | GMC 3 | C/HL | |
| 38 | C 45 | " | IPM 40 | GMC 5 | — | (b) |
| 39 | PIB 90 | " | — | — | — | |

PIB: Polyisobutylene pressure-sensitive adhesive
viscosity average molecular weight 990,000; 10 parts
viscosity average molecular weight 60,000; 15 parts
viscosity average molecular weight 1,260; 3 parts
plus
alicyclic petroleum resin: 7 parts
(softening point, 100° C.)
ES: estradiol
NP: nifedipine
KP: ketoprofen
CD: clonidine
Fatty acid esters: IPM (isopropyl myristate)
OP (octyl palmitate)
MITD (isotridecyl myristate)
EO (ethyl oleate)
Monoglycerides: GMC (glyceryl monocaprylate)
GMO (glyceryl monoleate)
GML (gryceryl monolaurate)
Crosslinking agent: C/HL (CORONATE HL: a trifunctional isocyanate, manufactured by Nippon Polyurethane Industry Co., Ltd.)
Remarks: (a) weak pressure-sensitivity; (b) cohesive failure The percutaneous absorption preparations obtained in the above Inventive Examples and Comparative Examples were subjected to the following stability test. The results are shown in Tables 5 to 7. Percutaneous absorption preparations obtained in Comparative Examples 10, 28 and 38 were not able to be used in the stability test because of cohesive failure due to lack in cohesive force of their pressure-sensitive adhesive layers, and the preparation of Comparative Example 8 was not subjected to the stability test because of its impractical weak pressure-sensitiveness.

Stability Test

Each sample was sealed using a packaging material and stored at 40° C. under a moisture condition of 75% RH to measure the drug content (per unit area) after 1, 3 and 6 months of the storage. The content after storage (%) was calculated based on the initial content (100%). In this test, appearance of the surface of each preparation was visually observed, and samples showing clearly irregular appearance due to crystal formation and the like were excluded from other tests.

TABLE 5

(Results of Inventive Examples)

| Ex. No. | Content stability | | | Appearance stability | | |
|---|---|---|---|---|---|---|
| | 1 month | 3 months | 6 months | 1 month | 3 months | 6 months |
| 1 | 100.4% | 99.8% | 99.8% | A | A | A |
| 2 | 100.0 | 99.9 | 99.7 | A | A | A |
| 3 | 101.1 | 99.6 | 99.8 | A | A | A |
| 4 | 99.7 | 99.9 | 99.8 | A | A | A |
| 5 | 99.6 | 100.2 | 100.0 | A | A | A |
| 6 | 101.4 | 100.0 | 100.7 | A | A | A |
| 7 | 100.9 | 100.1 | 99.7 | A | A | A |
| 8 | 101.2 | 99.9 | 99.7 | A | A | A |
| 9 | 101.4 | 100.0 | 99.6 | A | A | A |
| 10 | 99.9 | 99.9 | 99.8 | A | A | A |
| 11 | 99.6 | 100.1 | 99.7 | A | A | A |
| 12 | 99.8 | 99.7 | 99.7 | A | A | A |

Appearance stability
A: no change in appearance compared to the initial stage

TABLE 6

(Results of Comparative Examples)

| Ex. No. | Content stability | | | Appearance stability | | |
|---|---|---|---|---|---|---|
| | 1 month | 3 months | 6 months | 1 month | 3 months | 6 months |
| 1 | 100.0% | 101.3% | 100.3% | A | A | A |
| 2 | 99.6 | 100.0 | 99.7 | A | A | A |
| 3 | 100.1 | 99.8 | 99.9 | A | A | X |
| 4 | 100.1 | 101.2 | 100.2 | A | X | X |
| 5 | 100.0 | 99.1 | 96.8 | A | A | A |
| 6 | 100.8 | 98.3 | 96.0 | A | A | A |
| 7 | 100.0 | 101.1 | 100.0 | A | A | B |
| 9 | 99.9 | 99.9 | 99.7 | A | A | A |
| 11 | 101.1 | 101.0 | 100.4 | B | B | B |
| 12 | 101.0 | 100.0 | 101.2 | A | A | A |
| 13 | 99.9 | 99.6 | 99.9 | A | A | X |
| 14 | 100.0 | 99.8 | 100.6 | A | X | X B |
| 15 | 99.8 | 97.0 | 94.9 | A | A | A |
| 16 | 101.1 | 98.6 | 94.9 | A | A | A |
| 17 | 101.3 | 99.9 | 98.9 | A | A | A |
| 18 | 102.0 | 101.8 | 101.9 | A | A | A |
| 19 | 99.7 | 101.1 | 101.3 | B | B | B |

Appearance stability
A: no change in appearance compared to the initial stage
B: mottles due to partial formation of crystals
X: frequent exudation of fatty acid ester from the side

TABLE 7

(Results of Comparative Examples)

| Ex. No. | Content stability | | | Appearance stability | | |
|---|---|---|---|---|---|---|
| | 1 month | 3 months | 6 months | 1 month | 3 months | 6 months |
| 20 | 99.9% | 99.8% | 99.6% | A | A | A |
| 21 | 100.0 | 98.9 | 98.8 | A | A | A |
| 22 | 100.6 | 99.0 | 98.7 | A | A | A |
| 23 | 101.6 | 96.4 | 92.1 | A | A | A |
| 24 | 102.2 | 98.4 | 96.9 | A | A | A |
| 25 | 99.9 | 99.9 | 98.0 | A | A | A |
| 26 | 100.5 | 100.0 | 100.1 | A | A | A |
| 27 | 99.6 | 99.8 | 99.5 | A | A | A |
| 29 | 99.9 | 99.9 | 100.1 | A | B | B |
| 30 | 100.1 | 100.1 | 99.0 | A | A | A |
| 31 | 102.2 | 101.2 | 100.0 | A | A | B |
| 32 | 101.1 | 98.9 | 99.2 | A | A | B |
| 33 | 100.0 | 98.5 | 96.2 | A | A | A |
| 34 | 99.9 | 98.6 | 95.9 | A | A | A |
| 35 | 99.9 | 99.9 | 100.0 | A | A | B |

TABLE 7-continued (Results of Comparative Examples)

| Ex. No. | Content stability | | | Appearance stability | | |
|---|---|---|---|---|---|---|
| | 1 month | 3 months | 6 months | 1 month | 3 months | 6 months |
| 36 | 99.9 | 100.1 | 100.5 | A | A | A |
| 37 | 98.9 | 101.3 | 100.2 | A | A | A |
| 39 | 102.1 | 103.2 | 103.1 | B | B | B |

Appearance stability
A: no change in appearance compared to the initial stage
B: mottles due to partial formation of crystals
X: frequent exudation of fatty acid ester from the side As is apparent from the results shown in the above tables, samples of Comparative Examples 3 to 7, 13 to 16, 19, 23, 24, 29, 31 to 35 and 39 are inferior in at least one of the content stability and the appearance stability. Next, the following tests were carried out using selected samples of Inventive and Comparative Examples which were relatively stable in the above stability test. The results are shown in Tables 8 and 9.

Adhesive Force Test

Each sample cut into a tape-like shape of 24 mm in width was applied to a bakelite plate, closely contacted by adding 300 g of load with one reciprocation of a roller and then stripped off in a 180 degree direction at a rate of 300 mm/min to measure its adhesive force (peeling strength).

Skin Adhesive Force Test

Each sample cut into a shape of 12 mm in width and 50 mm in length was applied to the inner part of the lower arm of each of five volunteers for 6 hours and then stripped off in a 180 degree direction at a rate of 100 mm/min to measure its skin adhesive force (peeling strength). In the case of Inventive Examples 10 to 12 and Comparative Examples 30, 36 and 37 in which clonidine was used as the drug for percutaneous absorption, respective placebo preparations containing no clonidine were prepared and used in the test.

In this test, peeled removal of corneous cells was hardly found in samples of Inventive Examples. On the other hand, each sample of Comparative Examples caused peeling of corneous cells, clearly showing that the correlation strength among corneous cells was smaller than the interfacial adhesive force. In consequence, the value of each Comparative Example shown in Tables 8 and 9 is correlation strength among corneous cells.

Amount of Corneum Peeled

Each sample cut into a shape of 12 mm in width and 50 mm in length was applied to the inner part of the lower arm of each of five volunteers for 6 hours and then stripped off. The resulting sample was soaked for 24 hours in the following dyeing solution and then washed with distilled water to carry out dyeing of the peeled corneous cells. Since the dyeing solution used in this test permeates into the backing-constituting non-woven fabric, the backing was replaced by a single layer of a polyester film having a thickness of 9 μm. In the case of Inventive Examples 10 to 12 and Comparative Examples 30, 36 and 37 in which clonidine was used as the drug for percutaneous absorption, respective placebo preparations containing no clonidine were prepared and used in the test.

| Dyeing solution composition: | Gentian Violet | 1.0% |
|---|---|---|
| | Brilliant Green | 0.5% |
| | Distilled water | 98.5% |

Each of the thus dyed samples was cut into a size of 12 mm×5 mm and dipped in 5 ml of 1% sodium dodecyl sulfate aqueous solution for a whole day and night to extract the pigments from the adhered corneous cells, and absorbance (595 nm) of the extract was measured using a spectrophotometer. Each sample which was not applied to the skin surface was used as a control sample and subjected to the same extraction operation to calculate the absorbance as a differential spectrum between the control and test samples. Namely, higher measured absorbance indicates larger amount of peeled corneous cells.

In this test, a good correlation was found between the number of peeled corneous cells counted under a stereoscope and the absorbance described above.

Degree of Pain

Each sample cut into a size of 5 cm² was applied to the inner part of the upper arm of each of five volunteers for 1 hour and then peeled off to measure degree of pain at the time of peeling. The degree of pain was evaluated based on the following criteria to obtain average values.

1: no pain
2: feel pain
3: slightly painful
4: painful
5: strongly painful

TABLE 8

(Results of Inventive Examples)

| Ex. No. | Adhesive force (g) | Skin adhesive force (g) | Amount of corneum peeled (abs.) | Degree of pain |
|---|---|---|---|---|
| 1 | 115 | 49 | 0.40 | 1.0 |
| 2 | 130 | 55 | 0.52 | 1.2 |
| 3 | 121 | 50 | 0.53 | 1.2 |
| 4 | 129 | 40 | 0.51 | 1.2 |
| 5 | 135 | 51 | 0.36 | 1.2 |
| 6 | 130 | 43 | 0.30 | 1.0 |
| 7 | 133 | 52 | 0.49 | 1.2 |
| 8 | 140 | 58 | 0.38 | 1.4 |
| 9 | 144 | 49 | 0.48 | 1.2 |
| 10 | 118 | 36 | 0.30 | 1.0 |
| 11 | 109 | 32 | 0.39 | 1.0 |
| 12 | 121 | 41 | 0.38 | 1.0 |

TABLE 9

(Results of Comparative Examples)

| Ex. No. | Adhesive force (g) | Skin adhesive force (g) | Amount of corneum peeled (abs.) | Degree of pain |
|---|---|---|---|---|
| 1 | 144 | (*1) | — | — |
| 2 | 120 | 39 | 0.44 | 1.0 |
| 9 | 265 | 50 | 1.20 | 3.6 |
| 12 | 139 | 41 | 0.46 | 1.0 |
| 17 | 120 | 43 | 0.40 | 1.0 |
| 18 | 250 | 56 | 1.44 | 4.0 |
| 20 | 115 | 36 | 0.41 | 1.0 |
| 21 | 118 | (*1) | — | — |
| 22 | 146 | 42 | 0.36 | 1.2 |
| 25 | 130 | 46 | 0.39 | 1.0 |
| 26 | 320 | 49 | 1.60 | 4.8 |
| 27 | 215 | 51 | 1.38 | 4.2 |
| 30 | 109 | 38 | 0.39 | 1.0 |

TABLE 9-continued (Results of Comparative Examples)

| Ex. No. | Adhesive force (g) | Skin adhesive force (g) | Amount of corneum peeled (abs.) | Degree of pain |
|---|---|---|---|---|
| 36 | 334 | 46 | 1.40 | 4.0 |
| 37 | 198 | 52 | 1.20 | 3.6 |

(*1): not measurable due to too many peeling of corneous cells

As is apparent from the results shown in Tables 8 and 9, the samples of the present invention have proper adhesive force and cause smaller amount of corneous cells and degree of pain when peeled off. The samples of Comparative Examples, on the other hand, cause a large amount of peeled corneous cells and are painful when peeled off. In the case of the samples of Comparative Examples, the skin adhesive force does not signify adhesive force on the surface of the skin but indicates peeling strength, because these samples cause peeling of corneous cells from the skin surface, so that the measured values themselves are not so large.

On the basis of the test results shown in Table 9, samples of Comparative Examples 9, 18, 26, 27, 36 and 37 showing large quantities of peeled corneous cells and samples of Comparative Examples 1 and 21 showing too many peeling of corneous cells were excluded, and other samples showing relatively good results were used in the following rabbit adhesion test to measure blood drug levels. The results are shown in Tables 10 to 13.

Rabbit Adhesion Test (1) Transfer Amount of Estradiol (Table 10)

Each of the percutaneous absorption preparations containing estradiol was cut into a size of 20 cm² (40 mm×50 mm), adhered to a previously hair-clipped dorsal part of a rabbit and then peeled off 48 hours thereafter. The transfer amount was calculated based on the quantitative change (decreased amount) of estradiol before and after the application of each percutaneous absorption preparation.

TABLE 10

| | Transfer Amount of Estradiol |
|---|---|
| Inventive Example 1 | 1,440 (μg/20 cm²) |
| Inventive Example 2 | 1,600 (μg/20 cm²) |
| Inventive Example 3 | 1,680 (μg/20 cm²) |
| Comparative Example 2 | 1,250 (μg/20 cm²) |

(2) Blood Drug Level (Tables 11 to 13)

Each of the samples was adhered to a previously hair-clipped dorsal part of a rabbit, and blood samples were collected in 2 ml portions 1, 2, 4, 6 and 8 hours thereafter to measure the blood drug level by a gas chromatography. In this case, each of the samples in which clonidine was used as the drug for percutaneous absorption was made into a size of 3 cm² (17.3mm square), and other samples were made into a size of 50 cm² (70.7 mm square).

TABLE 11

| | Rabbit blood level test | |
|---|---|---|
| | C max (ng/ml) | T max (h) |
| Inventive Examples | | |
| 4 | 285 | 4.0 |
| 5 | 310 | 4.0 |

TABLE 11-continued

| | Rabbit blood level test | |
|---|---|---|
| | C max (ng/ml) | T max (h) |
| 6 | 315 | 4.0 |
| Comparative Examples | | |
| 12 | 210 | 6.0 |
| 17 | 230 | 6.0 |

TABLE 12

| | Rabbit blood level test | |
|---|---|---|
| | C max (ng/ml) | T max (h) |
| Inventive Examples | | |
| 7 | 2,650 | 2.0 |
| 8 | 2,970 | 2.0 |
| 9 | 2,880 | 2.0 |
| Comparative Examples | | |
| 20 | 2,110 | 4.0 |
| 22 | 1,840 | 4.0 |
| 25 | 2,250 | 2.0 |

TABLE 13

| | Rabbit blood level test | |
|---|---|---|
| | C max (ng/ml) | T max (h) |
| Inventive Examples | | |
| 10 | 18 | 6.0 |
| 11 | 26 | 6.0 |
| 12 | 30 | 6.0 |
| Comparative Example | | |
| 30 | 13 | 6.0 |

As is apparent from the results shown in Tables 10 to 13, drugs are quickly absorbed and their percutaneous absorption is improved by the samples of the present invention.

While the invention has been described in detail with reference to specific embodiments, it will be apparent to one skilled in the art that various changes and modifications can be made to the invention without departing from its spirit and scope.

What is claimed is:

1. A percutaneous absorption preparation comprising a backing and a pressure-sensitive adhesive layer containing a drug for percutaneous absorption formed on one side of the backing, wherein the pressure-sensitive adhesive layer contains (1) an acrylic copolymer prepared by copolymerization of a monomer mixture comprising a (meth)acrylic acid alkyl ester and a functional monomer as essential components, said ;functional monomer capable of being polymerized with the (meth) acrylic acid alkyl ester (2) a fatty acid ester comprising a higher fatty acid having 12 to 16 carbon atoms and a lower monohydric alcohol having 1 to 4 carbon atoms, (3) a monoglyceride comprising a higher fatty acid having 8 to 10 carbon atoms and glycerol and (4) a drug for percutaneous absorption (excluding isosorbide dinitrate), and the pressure-sensitive adhesive layer is crosslinked.

2. The percutaneous absorption preparation of claim 1 wherein the total content of said fatty acid ester and monoglyceride is within the range of from 60 to 200 parts by weight per 100 parts by weight of said acrylic copolymer.

3. The percutaneous absorption preparation of claim 1 wherein the content ratio (by weight) of said fatty acid ester to said monoglyceride is within the range of from 1:0.05 to 1:0.25.

4. The percutaneous absorption preparation of claim 1 wherein said drug for percutaneous absorption is an estrogen.

5. The percutaneous absorption preparation of claim 1 wherein said backing is a porous film or a laminate of a porous film and a non-porous plastic film, and the pressure-sensitive adhesive layer is formed on the porous film side.

* * * * *